US010493377B1

(12) United States Patent
Ferraro et al.

(10) Patent No.: US 10,493,377 B1
(45) Date of Patent: Dec. 3, 2019

(54) BIOMASS EXTRACTION AND CENTRIFUGATION SYSTEMS AND METHODS

(71) Applicant: Heinkel Filtering Systems, Inc., Swedesboro, NJ (US)

(72) Inventors: Alan Ferraro, Swedesboro, NJ (US); Bob Edwards, Swedesboro, NJ (US); Thomas Ahrens, Besigheim (DE)

(73) Assignee: Heinkel Filtering Systems, Inc., Swedesboro, NJ (US)

( * ) Notice: Subject to any disclaimer, the term of this patent is extended or adjusted under 35 U.S.C. 154(b) by 0 days.

(21) Appl. No.: 16/286,134

(22) Filed: Feb. 26, 2019

Related U.S. Application Data (60) Provisional application No. 62/802,163, filed on Feb. 6, 2019.

(51) Int. Cl.
| | |
|---|---|
| *B01D 11/02* | (2006.01) |
| *B01D 21/26* | (2006.01) |
| *A61K 31/352* | (2006.01) |
| *A61K 36/185* | (2006.01) |
| *C12C 3/08* | (2006.01) |

(52) U.S. Cl.
CPC ........ *B01D 11/0288* (2013.01); *A61K 31/352* (2013.01); *A61K 36/185* (2013.01); *B01D 21/262* (2013.01); *C12C 3/08* (2013.01); *A61K 2236/33* (2013.01); *A61K 2236/53* (2013.01)

(58) Field of Classification Search
CPC .............. B01D 11/0288; B01D 21/262; B01D 11/0269; B01D 11/028; B01D 21/26; A61K 36/185; A61K 31/352; A61K 2236/33; A61K 2236/53; C12C 3/00; C12C 3/08
See application file for complete search history.

(56) References Cited

U.S. PATENT DOCUMENTS

| | | |
|---|---|---|
| 3,973,984 A | 8/1976 | Hentschel |
| 5,195,939 A | 3/1993 | Gingras |
| 5,591,340 A | 1/1997 | Meikrantz |
| 6,059,712 A | 5/2000 | Corlett |
| 7,384,557 B2 * | 6/2008 | Phillips .............. C10G 1/04 196/14.52 |

(Continued)

FOREIGN PATENT DOCUMENTS

| | | |
|---|---|---|
| CN | 101972715 A | 2/2011 |
| CN | 204111719 U | 1/2015 |

(Continued)

OTHER PUBLICATIONS

Delta Separations; Centrifuge Utility Platform; Downloaded on Jan. 8, 2019 from https://www.deltaseparations.com/extraction/.

(Continued)

*Primary Examiner* — David C Mellon (57) ABSTRACT

Many embodiments described herein facilitate continuous biomass extraction and centrifugation. The biomass extraction and centrifugation system may include biomass and solvent feed tanks, a plurality of vessels, and a centrifuge. The biomass and solvent feed tanks may be fluidly coupled to the plurality of vessels, which may in turn be fluidly coupled to the centrifuge. In this manner, the system may be arranged and configured to run in a continuous manner with a substantially constant and repeatable extraction result.

20 Claims, 8 Drawing Sheets

(56) References Cited

U.S. PATENT DOCUMENTS

| | | |
|---|---|---|
| 8,728,215 B2 | 5/2014 | Manning |
| 8,895,078 B2 | 11/2014 | Mueller |
| 8,998,789 B2 | 4/2015 | Toi |
| 9,732,009 B2 | 8/2017 | Raber |
| 9,808,494 B2 | 11/2017 | Barringer |
| 2011/0003888 A1* | 1/2011 | Kuhrts .................... C12C 3/08 514/456 |
| 2011/0263030 A1 | 10/2011 | Kim |
| 2013/0079531 A1 | 3/2013 | Barringer |
| 2015/0126754 A1 | 5/2015 | Cid |
| 2015/0353865 A1 | 12/2015 | Poon |
| 2017/0080422 A1 | 3/2017 | Maaskant |
| 2017/0106030 A1* | 4/2017 | Aari .................... A61K 36/185 |
| 2018/0147247 A1 | 5/2018 | Ivanov |

FOREIGN PATENT DOCUMENTS

| | | |
|---|---|---|
| CN | 105535111 A | 5/2016 |
| CN | 106011207 A | 10/2016 |

OTHER PUBLICATIONS

Rousselet Robatel; Cannabis Refining; Downloaded on Jan. 8, 2019 from http://www.rousselet-robatel.com/applications/cannabis-refining/.

Delta Separations; Delta Separations CUP; Retrieval date Nov. 29, 2018; Downloaded from https://www.youtube.com/watch?v=PfgFh6ksBKs&feature=youtu.be; Prior art at least as of Jun. 19, 2017.

Medium; Cannabis Tech Hardware Wunderkind; Retrieval date Nov. 29, 2018; Downloaded from https://medium.com/@Pustejovsky/cannabis-tech-hardware-wunderkind-56946f744d1c; Prior art at least as of Nov. 8, 2017.

\* cited by examiner

BIOMASS EXTRACTION AND CENTRIFUGATION SYSTEMS AND METHODS

CROSS-REFERENCE TO RELATED APPLICATIONS

This application claims the benefit of U.S. Provisional Patent Application No. 62/802,163; filed Feb. 6, 2019; and entitled BIOMASS EXTRACTION AND CENTRIFUGATION SYSTEMS AND METHODS; the entire contents of which are incorporated herein by reference.

BACKGROUND

Field

Various embodiments disclosed herein relate to systems and methods for biomass extraction and centrifugation. Certain embodiments relate to cannabis and hemp extraction and centrifugation.

Description of Related Art

Biomass extraction, specifically the extraction of essential oils from plant materials, is a practice that can be traced back as early as the $13^{th}$ century. Though medicine in much of the world has advanced beyond dependency on essential oils, and the techniques of biomass extraction are significantly more complex, the general concept remains the same. The main components of an extraction process are biomass material, an extracting element, and a method of separation. Early extraction methods used heat to extract compounds from biomass materials, and collected and condensed the resultant steam to form the extraction result. More current and complex methodologies employ chemical solvents and intricate machinery, but reach the same ultimate goal of collecting desired compounds from biomass materials. Biomass extraction is used across a variety of industries, including the pharmaceutical, nutraceutical, cosmetic and perfume, and agricultural industries.

Biomass extraction techniques are typically directed to the goal of maximizing components extracted from a biomass material in the shortest period of time possible, while maintaining a high quality extraction result. Biomass extraction has traditionally been a manual, labor-intensive, and relatively slow process. Different extraction techniques use a variety of solvents, including butane, carbon dioxide, and ethanol, to extract desired components from a multitude of biomass materials. While different solvents are appropriate for different biomass materials, in recent years ethanol has been used increasingly for cannabis extraction. One common method of cannabis extraction involves a cylindrical filter bag of cannabis inserted in a vertical centrifuge; the centrifuge is then flooded with ethanol and agitated to extract components of the cannabis, including cannabidiol (CBD) and/or tetrahydrocannabinol (THC). CBD and/or THC are desired components of cannabis because both have numerous health benefits, including pain relief, appetite stimulation, and muscle spasm suppression. CBD has additional health benefits that will be discussed later in the disclosure. This common method is continued by draining the centrifuge of ethanol, spinning dry the filter bag of cannabis, and removing the filter bag from the centrifuge. While this method is effective, it is slow, labor intensive, and requires manual operation. Therefore, there is a need for improved extraction systems and methods to reduce both the time and labor requirements of current extraction practices.

SUMMARY

The current invention advances biomass extraction and centrifugation practices in a novel way by facilitating a continuous and minimally labor-intensive process.

This disclosure includes systems and methods for biomass extraction and centrifugation. Some embodiments include a biomass extraction and centrifugation system comprising a biomass feed tank, a solvent feed tank, a plurality of vessels, and a centrifuge. Each vessel of the plurality of vessels may be fluidly coupled to both the biomass feed tank and solvent feed tank, and the centrifuge may be fluidly coupled to each vessel of the plurality of vessels. In some embodiments, each vessel is configured to hold a slurry comprising a biomass and a solvent, and the centrifuge is configured to separate the slurry into a first extract discharge and a first waste discharge. In several embodiments, the biomass includes at least one of cannabis and hemp. The system may be sized and configured such that the fluid coupling between the centrifuge, the plurality of vessels, the biomass feed tank, and the solvent feed tank may enable the system to run in a continuous manner with a constant and repeatable extraction result.

In some embodiments, an amount and ratio of biomass to solvent is defined with respect to a batch size of the centrifuge. The ratio of biomass to solvent may be substantially constant to thereby ensure a repeatable process. In several embodiments, the solvent may comprise ethanol.

In some embodiments, each vessel of the plurality of vessels includes a cover that at least partially encloses each vessel. As well, each vessel of the plurality of vessels may further include a control valve that may send a respective slurry into the centrifuge. In several embodiments, each control valve opens and closes in response to an availability of the centrifuge.

Methods of continuously extracting and centrifuging biomass may include sending biomass from a biomass feed tank into a first vessel of a plurality of vessels, and sending solvent from a solvent feed tank into the first vessel. Methods may also include holding the biomass and solvent in the first vessel for a predetermined amount of time, wherein a first slurry of a first cycle may comprise the biomass and solvent. As well, methods may include extracting at least a portion of a biomass extraction from the first slurry of the first cycle, and centrifuging and separating, via a centrifuge fluidly coupled to the plurality of vessels, the first slurry of the first cycle into a first extract discharge and a first waste discharge.

In some embodiments, methods further comprise sending biomass from the biomass feed tank into a second vessel of the plurality of vessels and sending solvent from the solvent feed tank into the second vessel. Methods may also include holding the biomass and solvent in the second vessel for the predetermined amount of time, wherein a second slurry of the first cycle comprises the biomass and solvent. Furthermore, methods may include extracting at least a portion of a biomass extraction from the second slurry of the first cycle, and centrifuging and separating, via the centrifuge, the second slurry of the first cycle into a second extract discharge and a second waste discharge. In several embodiments, methods include extracting at least the portion of the biomass extraction from the first slurry of the first cycle while simultaneously sending biomass and solvent into the second vessel.

In some embodiments, methods further comprise sending biomass from the biomass feed tank into a third vessel of the plurality of vessels and sending solvent from the solvent feed tank into the third vessel. Methods may also include holding the biomass and solvent in the third vessel for the predetermined amount of time, wherein a third slurry of the first cycle comprises the biomass and the solvent. As well, methods may comprise extracting at least a portion of a biomass extraction from the third slurry of the first cycle, and centrifuging and separating, via the centrifuge, the third slurry of the first cycle into a third extract discharge and a third waste discharge. In several embodiments, methods may further include sending biomass and solvent into the third vessel while simultaneously extracting at least the portion of the biomass extraction from the first slurry of the first cycle. As well, methods may include sending biomass and solvent into the third vessel while simultaneously extracting at least the portion of the biomass extraction from the second slurry of the first cycle.

In some embodiments, methods comprise sending biomass from the biomass feed tank into a fourth vessel of the plurality of vessels and sending solvent from the solvent feed tank into the fourth vessel. Methods may further include holding the biomass and the solvent in the fourth vessel for the predetermined amount of time, wherein a fourth slurry of the first cycle comprises the biomass and the solvent. As well, methods may comprise extracting at least a portion of a biomass extraction from the fourth slurry of the first cycle, and centrifuging and separating, via the centrifuge, the fourth slurry of the first cycle into a fourth extract discharge and a fourth waste discharge. In many embodiments, methods include sending biomass and solvent into the fourth vessel while simultaneously extracting at least one of at least the portion of the biomass extraction from the first slurry of the first cycle, at least the portion of the biomass extraction from the second slurry of the first cycle, and at least the portion of the biomass extraction from the third slurry of the first cycle.

In some embodiments, while extracting at least the portion of the biomass extraction from the fourth slurry of the first cycle, methods further comprise centrifuging and separating the first slurry of the first cycle via the centrifuge, sending biomass from the biomass feed tank into the first vessel for a second cycle, sending solvent from the solvent feed tank into the first vessel for a second cycle, and extracting at least a portion of a biomass extraction from a first slurry of the second cycle.

While extracting at least the portion of the biomass extraction from the fourth slurry of the first cycle, methods may include extracting at least a portion of a biomass extraction from the second slurry of the first cycle, centrifuging and separating the second slurry of the first cycle, sending biomass from the biomass feed tank into the second vessel for the second cycle, sending solvent from the solvent feed tank into the second vessel for the second cycle, and extracting at least a portion of a biomass extraction from a second slurry of the second cycle.

While extracting at least the portion of the biomass extraction from the fourth slurry of the first cycle, methods may further include extracting at least a portion of a biomass extraction from the third slurry of the first cycle, centrifuging and separating the third slurry of the first cycle, sending biomass from the biomass feed tank into the third vessel for a second cycle, and sending solvent from the solvent feed tank into the third vessel for a second cycle.

In some embodiments, while centrifuging and separating the fourth slurry of the first cycle, methods further comprise extracting at least a portion of a biomass extraction from the first slurry of the second cycle, extracting at least a portion of a biomass extraction from the second slurry of the second cycle, and extracting at least a portion of a biomass extraction from a third slurry of the second cycle. As well, methods may include sending biomass from the biomass feed tank into the fourth vessel of the plurality of vessels for the second cycle and sending solvent from the solvent feed tank into the fourth vessel for the second cycle.

Though a plurality of vessels comprising four vessels is used as an example throughout the specification, any suitable number of vessels may be used. A number of vessels in the plurality of vessels may be determined by both the predetermined amount of time for holding the biomass and solvent and centrifugation time to separate each slurry. In some embodiments, the number of vessels in the plurality of vessels is determined by an amount of biomass in the biomass feed tank, an amount of solvent in the solvent feed tank, and a capacity of the centrifuge.

In many embodiments, the sending, extracting, centrifuging, and separating steps repeat until at least one of the biomass and solvent feed tank is substantially empty.

BRIEF DESCRIPTION OF THE DRAWINGS

These and other features, aspects, and advantages are described below with reference to the drawings, which are intended to illustrate, but not to limit, the invention. In the drawings, like reference characters denote corresponding features consistently throughout similar embodiments. Various components in the drawings may not be drawn to scale.

DETAILED DESCRIPTION

Although certain embodiments and examples are disclosed below, inventive subject matter extends beyond the specifically disclosed embodiments to other alternative embodiments and/or uses, and to modifications and equivalents thereof. Thus, the scope of the claims appended hereto is not limited by any of the particular embodiments described below. For example, in any system or method disclosed herein, the acts or operations of the system or method may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, methods, and/or procedures described herein may be embodied as integrated components or as separate components.

For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

INDEX OF COMPONENTS

10—Biomass extraction and centrifugation system
12—Biomass feed tank
14—Solvent feed tank
16—Plurality of vessels
16a—First vessel
16b—Second vessel
18—Slurry
18a—First slurry
18b—Second slurry
20—Biomass
22—Solvent
24—Centrifuge
26—Extract discharge
26a—First extract discharge
26b—Second extract discharge
28—Waste discharge
28a—First waste discharge
28b—Second waste discharge
30—At least one of cannabis and hemp
40—Cover
42—Control valve

INTRODUCTION

Biomass extraction techniques have advanced far beyond the heat extraction of essential oils used in the 13$^{th}$ century. Biomass extraction is now a vital process across many industries and is used for the production of everyday goods, from prescription drugs to household cleaning supplies to perfume. Biomass extraction combines raw biomass materials with an extracting element, such as a solvent, to extract desired components from the raw materials, and uses a centrifuge to separate the raw material waste from the desired extraction result.

Cannabis extraction is one particular example of biomass extraction that has been gaining popularity in recent years as more states in the U.S. legalize marijuana, and the potential benefits of cannabis compounds become recognized, understood, appreciated, and accepted by the medical community. Traditional cannabis extraction and centrifugation processes use a vertical basket centrifuge, which, while effective in collecting CBD, is a slow and labor-intensive process.

This disclosure has remedied the deficiencies of the prior art by using, in many embodiments, a plurality of feed tanks and extraction vessels to continuously feed biomass and solvent into a centrifuge. With multiple feed tanks and vessels feeding biomass and solvent into the centrifuge this allows for a continuous process having significantly less downtime than prior art systems.

In some embodiments, the centrifuge used in the system and method discussed in this disclosure is an inverting filter centrifuge, which allows for a much higher production capacity than extraction and centrifugation from other types of centrifuges systems, such as a vertical basket centrifuge, which operates in a non-continuous way. Additionally, vertical basket centrifuge systems may, in some cases, require an upstream storage container to serve as a "staging area" for substances waiting to be centrifuged. The use of a vertical basket centrifuge with a storage container adds an extra step into the process, as biomass and solvent must be moved from their initial container, to the storage container, and finally to the centrifuge. An inverting filter centrifuge operates continuously and, as such, does not require an additional storage tank because substances can move directly to the centrifuge. This direct movement allows a biomass extraction and centrifugation process using an inverting filter centrifuge to move more quickly and efficiently than the same process using a vertical basket centrifuge. A vertical basket centrifuge also may have more difficulty discharging solids following centrifugation, adding another instance where the extraction and centrifugation process may be slowed down. Overall, a biomass extraction and centrifugation process using a continuous inverting filter centrifuge may move more quickly and efficiently than the same process carried out in a non-continuous way in a vertical basket centrifuge.

Existing biomass extraction methods are typically slow and require a large amount of manual labor, particularly in the case of cannabis extraction. Accordingly, there is a need to carry out biomass extraction on a high-scale production basis with minimal manual labor and maximum efficiency. The biomass extraction and centrifugation system and method of this disclosure solve the existing problems of biomass extraction through implementation of an automated and continuous process that allows for minimal manual labor, high efficiency, and high quantity and quality output. While this disclosure refers primarily to cannabis, it is important to realize that the teachings of this disclosure can be implemented across many industries to extract any desired components from almost any biomass.

Figure 1:
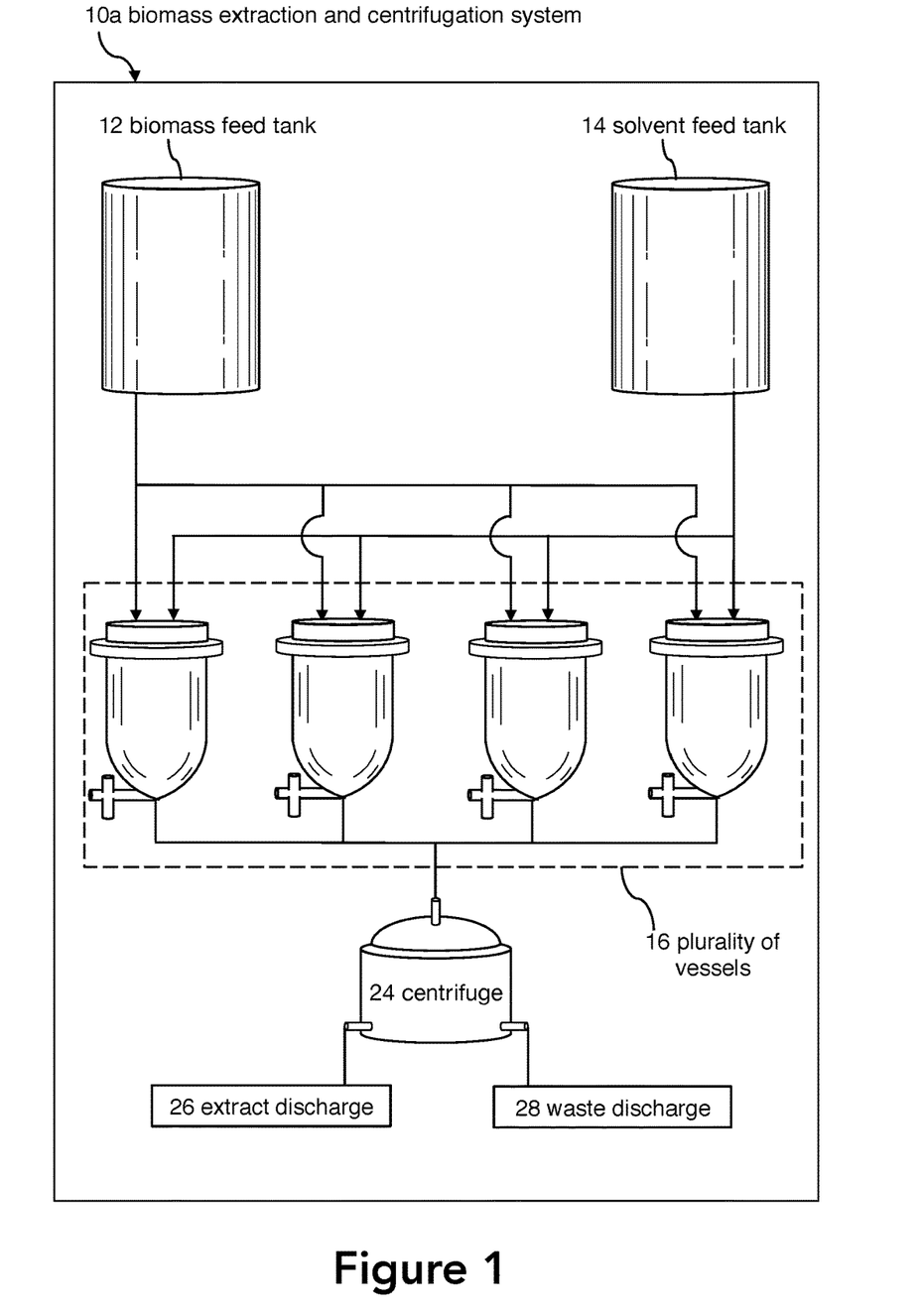
FIG. 1 illustrates a schematic view of a biomass extraction and centrifugation system, according to some embodiments.

Referring now to the figures, FIG. 1 illustrates a schematic view of a biomass extraction and centrifugation system 10a, and gives a general idea of the path of materials as they move through the extraction and centrifugation process. As shown, the system 10a may include a biomass feed tank 12 and a solvent feed tank 14. The biomass and solvent feed tanks 12, 14 may be fluidly coupled to a plurality of vessels 16, which in turn may be fluidly coupled to a centrifuge 24. The components of the system 10a may be fluidly coupled in order to create a closed system capable of continuously receiving raw ingredients and processing the ingredients to yield the desired biomass components, such as CBD and THC.

It should be noted that only marijuana contains substantial concentrations (15-40%) of THC, while hemp contains predominantly CBD with a nearly negligible concentration (0.3%) of THC. In an extraction where CBD is the desired extraction result and no psychoactive effects are sought, a user may be advised to choose hemp, rather than marijuana, as the biomass material. CBD and THC are both desired components for various uses, including as analgesic, appetite stimulant, and antispasmodic agents. CBD in particular has a multitude of other uses, including as an anti-inflammatory, antipsychotic, antiepileptic, anti-bacterial, and immunosuppressive agent, among others.

Accordingly, the system 10a may be arranged and configured to send biomass and solvent from feed tanks 12, 14 to the plurality of vessels 16. The biomass and solvent may comprise a slurry 18 in each vessel, and the plurality of vessels 16 may be arranged and configured to send the slurry 18 to a centrifuge 24. In some embodiments, the centrifuge 24 is an inverting filter centrifuge. Alternatively, the centrifuge 24 may be a peeler centrifuge. In order to yield the desired biomass components from the system 10a, the centrifuge 24 may separate the slurry 18 into an extract discharge 26, containing a desired biomass component, and a waste discharge 28, containing biomass waste. In some embodiments, the extract discharge 26 is released throughout the duration of operation of the centrifuge, and the waste discharge 28 is released once the centrifuge stops spinning.

In some embodiments, it is necessary to maintain a predetermined temperature or temperature range within each respective receptacle of the system 10a. Accordingly, the biomass feed tank 12, solvent feed tank 14, plurality of vessels 16, centrifuge 24, and/or the fluid coupling infrastructure may be jacketed and/or insulated. In this regard, maintaining the various components at a predetermined temperature may enhance the efficacy and accuracy of the process in producing the desired component(s), as well as reduce some common issues of some biomass extraction techniques, including heating of the biomass and/or biomass extraction during centrifugation.

Figure 2:
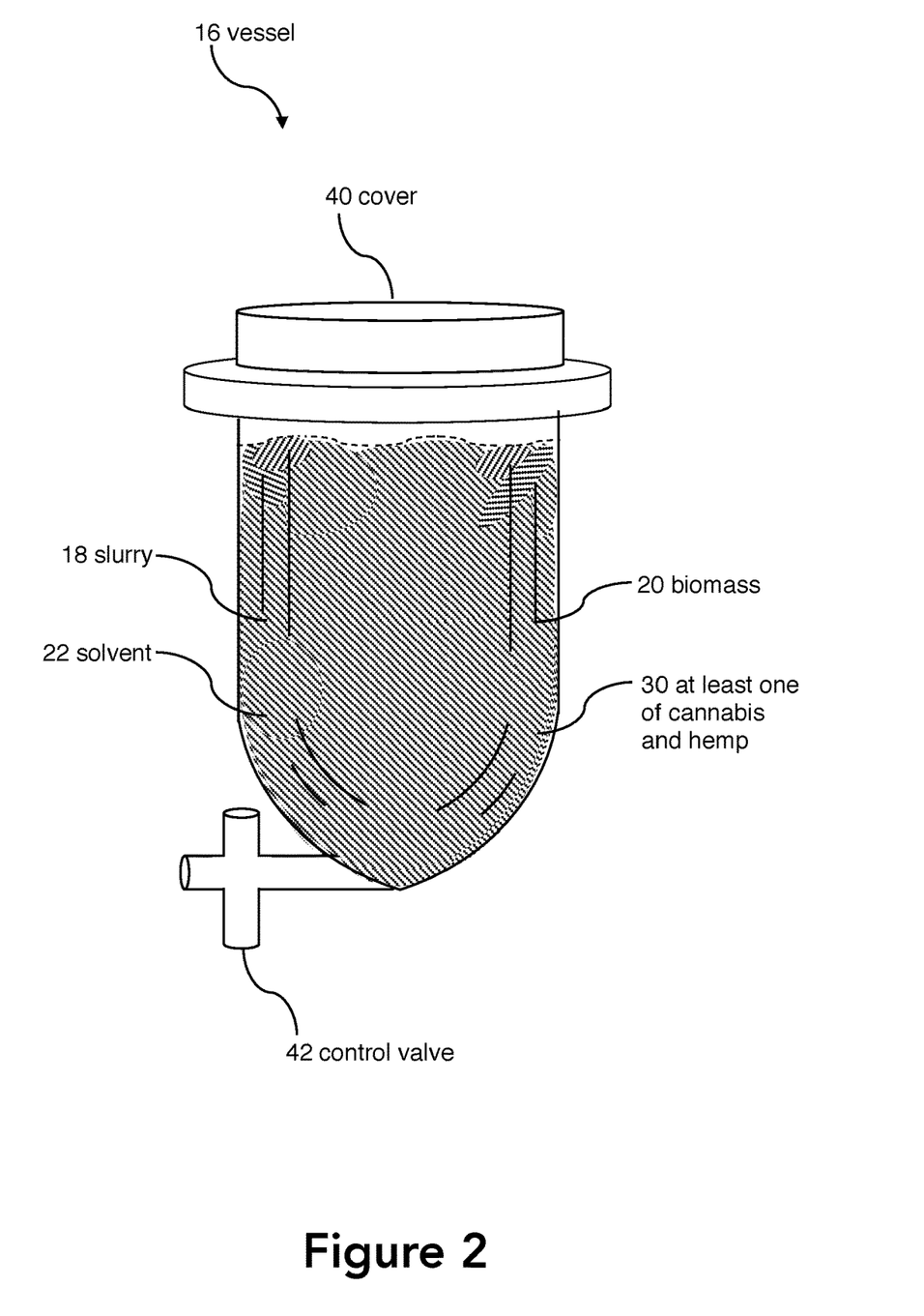
FIG. 2 illustrates a perspective view of a single vessel containing a slurry, according to some embodiments.

FIG. 2 illustrates a perspective view of a single vessel 16 containing a slurry 18, and shows the key components of the vessel 16 and the slurry 18, according to some embodiments. It should be appreciated that the slurry may comprise biomass 20 and solvent 22. In many embodiments, the biomass 20 comprises at least one of cannabis and hemp 30. The biomass 20 may alternatively comprise another biomass material, such as hops. The biomass 20 may be whole, ground, dried, frozen, or in another physical condition. For example, cannabis may be frozen upon harvesting as a preservative measure and may remain frozen until loaded into the biomass feed tank 12. In an embodiment where the biomass 20 comprises hops, the hops may be in whole leaf or pellet form, and, in some embodiments, are ground prior to loading into the biomass feed tank 12. In many embodiments, the solvent 22 comprises ethanol. Ethanol, when used as the solvent, may be maintained at a temperature range of −60° C. to −40° C., through jacketing and/or insulating as described above. However, in many embodiments, the systems and methods disclosed herein use other types of solvent, such as acetone, butanol, ethyl acetate, ethylene glycol, heptane, methanol, water, and the like, each of which may require a different optimal temperature range.

Additionally, in order to maintain more control over process parameters, each vessel 16 may comprise a cover(s) 40 to protect the contents of the vessel 16 and a control valve(s) 42 to regulate flow to and from each respective vessel 16. The cover(s) 40 may also aid in temperature regulation as a component of insulation for the vessel 16. In some embodiments, the cover(s) 40 is attached to the vessel 16 with a hinge, allowing the cover(s) 40 to be opened and closed. Alternatively, the cover(s) 40 may be completely removable from the vessel 16. In some embodiments, the cover(s) 40 includes an opening(s), such as a hole(s), to provide a connection(s) to the fluid coupling infrastructure in order to facilitate the transfer of biomass 20 and solvent 22 from the feed tanks 12, 14 into the vessel 16.

In many embodiments, the control valve(s) 42 opens and closes in response to an availability of the centrifuge 24. The centrifuge 24 may direct the control valve(s) 42 of the vessel 16 to open, thus releasing the slurry 18 from the vessel 16 to the centrifuge 24 without manual intervention from a system user. Once a slurry 18a of a first vessel 16a of the plurality of vessels 16 is centrifuged and separated, the centrifuge 24 may immediately indicate an availability and trigger the control valve 42 of a second vessel 16b of the plurality of vessels 16 to open and release a second slurry 18b from the vessel 16 to the centrifuge 24, thus allowing the second slurry 18 to proceed to centrifugation. This feature may allow the system to run in a continuous manner and maximize efficiency while minimizing the need for manual intervention, as well as virtually eliminating "down time" of the centrifuge.

While FIG. 1 (and the claims) illustrate the system 10a having four vessels 16, it should be appreciated that four vessels 16 is just one example to illustrate the general concept that the system 10a may include more than one vessel 16 to continuously feed slurry 18 to the centrifuge 24 so that the centrifuge 24 can continuously operate. Additionally, the system 10a may also include more than two feed tanks to thereby supply the system 10a with additional components beyond a biomass 20 and a solvent 22. Moreover, the system 10a may be arranged and configured to include more than one feed tank for each component being added to the system 10a. For example, the system 10a may include a plurality of biomass feed tanks 12 and a plurality of solvent feed tanks 14. Furthermore, while it is not shown in FIG. 2, in some embodiments one or more vessels 16 may comprise an agitator to thereby prevent the slurry 18 from sticking to a side wall of the vessel 16 and to ensure a high quality extraction. The agitator may work continuously for constant mixing or may operate intermittently for periods of mixing and rest while the slurry 18 is held in the vessel 16, as appropriate.

Figure 3A:
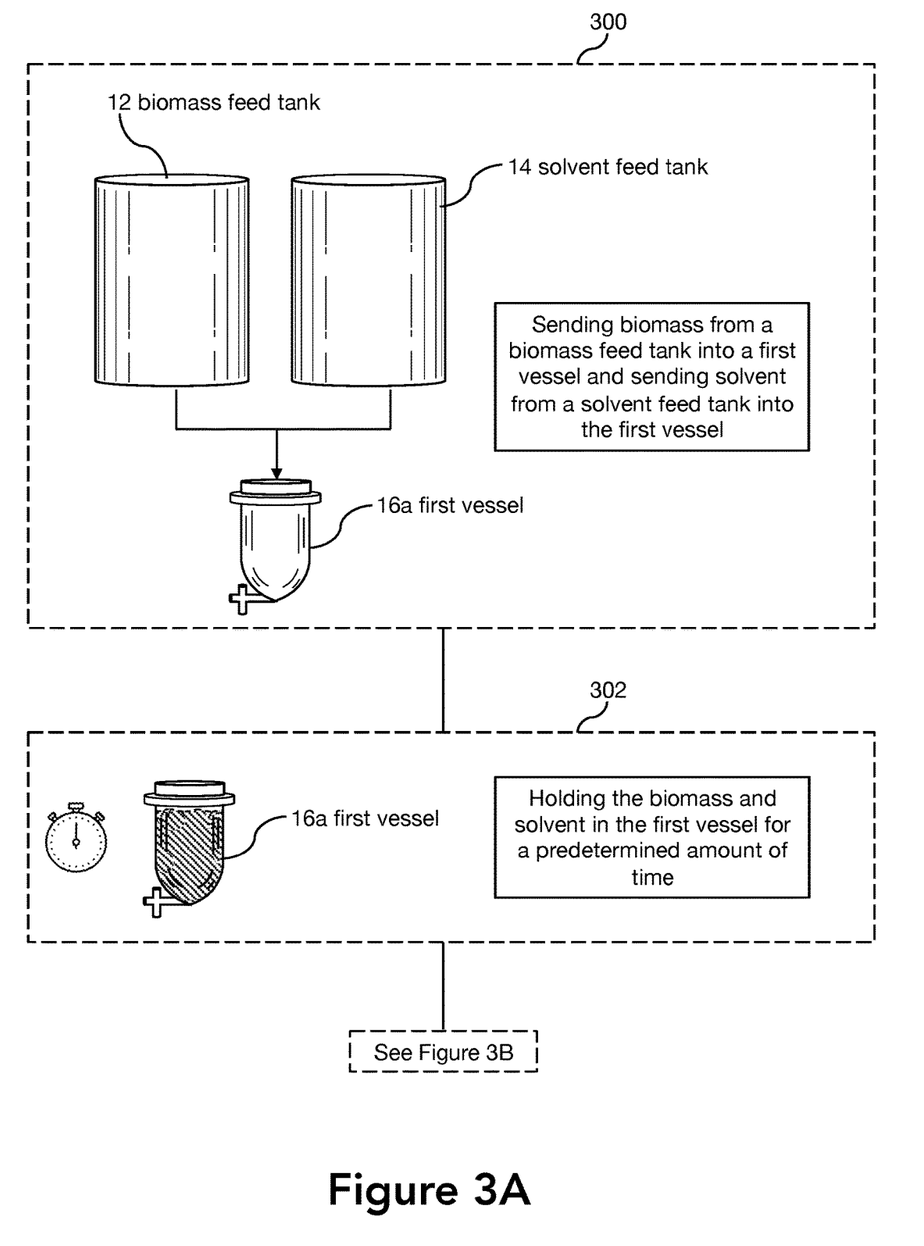
FIG. 3A illustrates a method of sending biomass and solvent into a first vessel and holding the biomass and solvent in the first vessel, according to some embodiments.
Figure 3B:
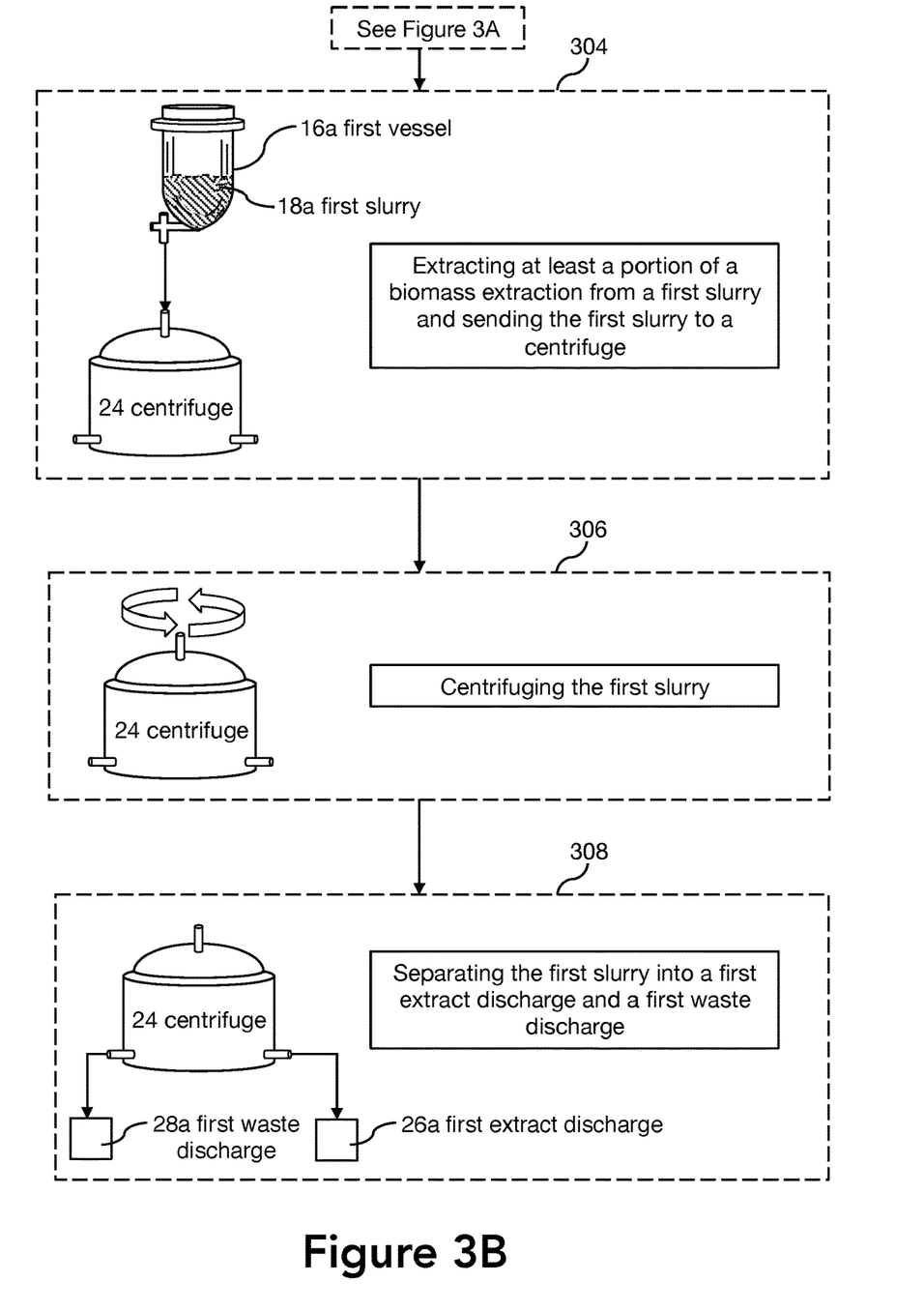
FIG. 3B illustrates a method of extracting a biomass extraction and centrifuging and separating a first slurry, according to some embodiments.

FIGS. 3A and 3B illustrate a method of continuously extracting and centrifuging biomass in a first vessel 16a, whereby FIG. 3A shows the first two steps of the method and FIG. 3B is a continuation of FIG. 3A to demonstrate the proceeding steps of the method. In some embodiments, the method includes sending biomass 20 from a biomass feed tank 12 into the first vessel 16a and sending solvent 22 from a solvent feed tank 14 into the first vessel 16a (at step 300). The biomass 20 and solvent 22 may then be held in the first vessel 16a for a predetermined amount of time (at step 302). In many embodiments, the biomass 20 and solvent 22 may form a first slurry 18a in the first vessel 16a. The method may further comprise extracting at least a portion of a biomass extraction from the first slurry 18a and sending the first slurry 18a to a centrifuge 24 (at step 304). Additionally, the method may include centrifuging the first slurry 18a (at step 306) and separating the first slurry 18a into a first extract discharge 26a and a first waste discharge 28a (at step 308). In some embodiments, the centrifuge 24 operates at 2300 RPM.

In some embodiments, sending biomass 20 and solvent 22 from the feed tanks 12, 14 to a first vessel 16a happens simultaneously. Alternatively, the step of sending biomass 20 may happen subsequent to sending solvent 22, and/or vice versa. In some embodiments, a pump operating at 50 gallons/minute performs the sending step 300. The configuration of the various embodiments of the system 10a, as well as other particular conditions surrounding a biomass extraction process, may determine the exact manner of sending biomass 20 and solvent 22 into the plurality of vessels 16.

The system 10a may be arranged and configured such that a number of vessels 16 may be determined based on an amount of time it takes to process and centrifuge the components to yield the desired biomass extraction (e.g., CBD and/or THC). For example, in some embodiments, sending biomass 20 and solvent 22 from the feed tanks 12, 14 to the respective vessel 16, takes a known amount of time, such as less than one minute, one minute, two minutes, four minutes, any amount of time greater than one minute, and the like. In some embodiments, the known amount of time to send the biomass 20 and solvent 22 from the feed tanks 12,14 to the respective vessel 16 is approximately equal to an amount of time to run the centrifuge. The "time to run the centrifuge" may include the steps of feeding and discharging the centrifuge 24, as well as the actual spin time. The time to run the centrifuge may be longer when the biomass 20 comprises a heavier type of biomass 20 (e.g. when the biomass 20 is a type other than cannabis or hemp). In this regard, while the centrifuge 24 is under operation, another vessel 16 may simultaneously receive ingredients from the feed tanks 12, 14 to thereby process a subsequent batch of biomass extraction. In many embodiments, the vessel 16 that previously held the slurry 18 now undergoing centrifugation may receive ingredients from feed tanks 12, 14 to prepare for a second cycle of the extraction process. The number of vessels 16 and setup arrangements will be discussed further with regards to FIG. 5.

The first slurry 18a may form when the biomass 20 and solvent 22 are combined in the first vessel 16a, and in some embodiments the first slurry 18a held in the first vessel 16a for a predetermined amount of time. In many embodiments, the predetermined amount of time is about 12 minutes. The exact length of the predetermined amount of time may vary based on the type and amount of biomass 20, the type and amount of solvent 22, the size of each vessel 16, etc., and may be between six and twenty minutes. In some embodiments, the predetermined amount of time may include periods of mixing the first slurry 18a.

The first slurry 18a may comprise a specific ratio of biomass 20 to solvent 22. In many embodiments, the typical ratio of biomass 20 to solvent 22 is 1:5. The amount and ratio of biomass 20 to solvent 22 input into the system 10a may depend on the type, as well as the particular physical and chemical properties of both the biomass 20 and the solvent 22 used in the system 10a. Furthermore, the amount of each biomass 20 and solvent 22 may be determined based on the size of any component or vessel within the system 10a, including the biomass and solvent feed tanks 12, 14. For example, in some embodiments, the amount and ratio is defined with respect to a batch size of the centrifuge 24. The batch size of the centrifuge 24 may also aid in the determination of the appropriate size and number of vessels within the plurality of vessels 16. In several embodiments, the ratio of biomass 20 to solvent 22 is substantially constant to ensure a repeatable process, as well as a consistent and repeatable extraction result. The repeatable and consistent nature of the biomass 20 to solvent 22 ratio and the extraction result may contribute to the continuous manner in which the method operates, through each vessel of the plurality of vessels 16 and each cycle of the extraction and centrifugation process.

As the first slurry 18a is held in the first vessel 16a, biomass extraction may take place. This extraction may occur as the biomass 20 reacts with the solvent 22, releasing components of the biomass 20. For example, in an embodiment where the biomass 20 is cannabis and the solvent 22 is ethanol, CBD may be extracted from the raw cannabis material into the slurry 18. After extraction over the predetermined amount of time, the first slurry 18a may be sent to a centrifuge 24 and thereby centrifuged to result in the separation of the first slurry 18a into a first extract discharge 26a and a first waste discharge 28a. In this cannabis/ethanol embodiment, the first extract discharge 26a comprises a "crude oil" of CBD and ethanol, and the first waste discharge 28a comprises cannabis with most of the CBD (and any excess ethanol) removed. In other embodiments, the first extract discharge 26a comprises the "crude oil" biomass extract with the solvent, and the first waste discharge 28a comprises the biomass with most of the extracted component and excess solvent removed. In some embodiments, a small amount of the desired extract component and solvent may remain absorbed by and/or integrated with the biomass waste. This possible residual moisture after centrifugation may be about 2%. The extract discharge may then undergo further filtering or purification methods to remove the solvent and result in a substantially pure form of the desired component.

In many embodiments, the transfer of material between the biomass and solvent feed tanks 12, 14, the plurality of vessels 16, and the centrifuge 24 is completed via a fluid coupling infrastructure. The fluid coupling infrastructure may define series of fluid connections amongst any of the components described herein. For example, the infrastructure may comprise pipes, tubes, pumps, any components suitable for the transfer of biomass and solvent materials, and the like. As previously discussed, the fluid coupling infrastructure may be jacketed and/or insulated for temperature regulation. The fluid coupling infrastructure may be made from at least one of plastic, metal, rubber, and any other suitable material, as may the feed tanks 12, 14, each vessel of the plurality of vessels 16, and the centrifuge 24, as well as respective elements of each component of the system 10a.

Figure 4A:
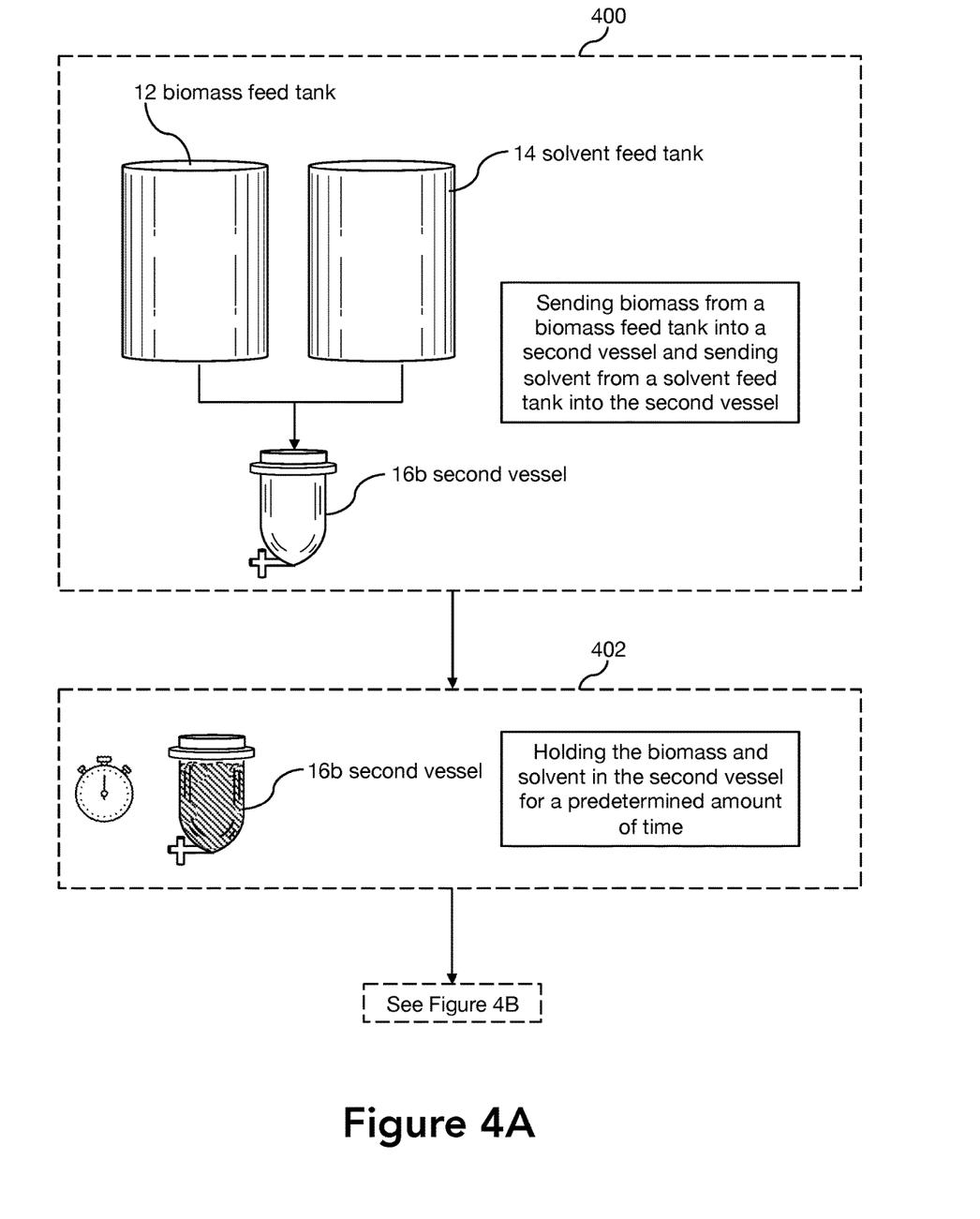
FIG. 4A illustrates a method of sending biomass and solvent into a second vessel and holding the biomass and solvent in the second vessel, according to some embodiments.
Figure 4B:
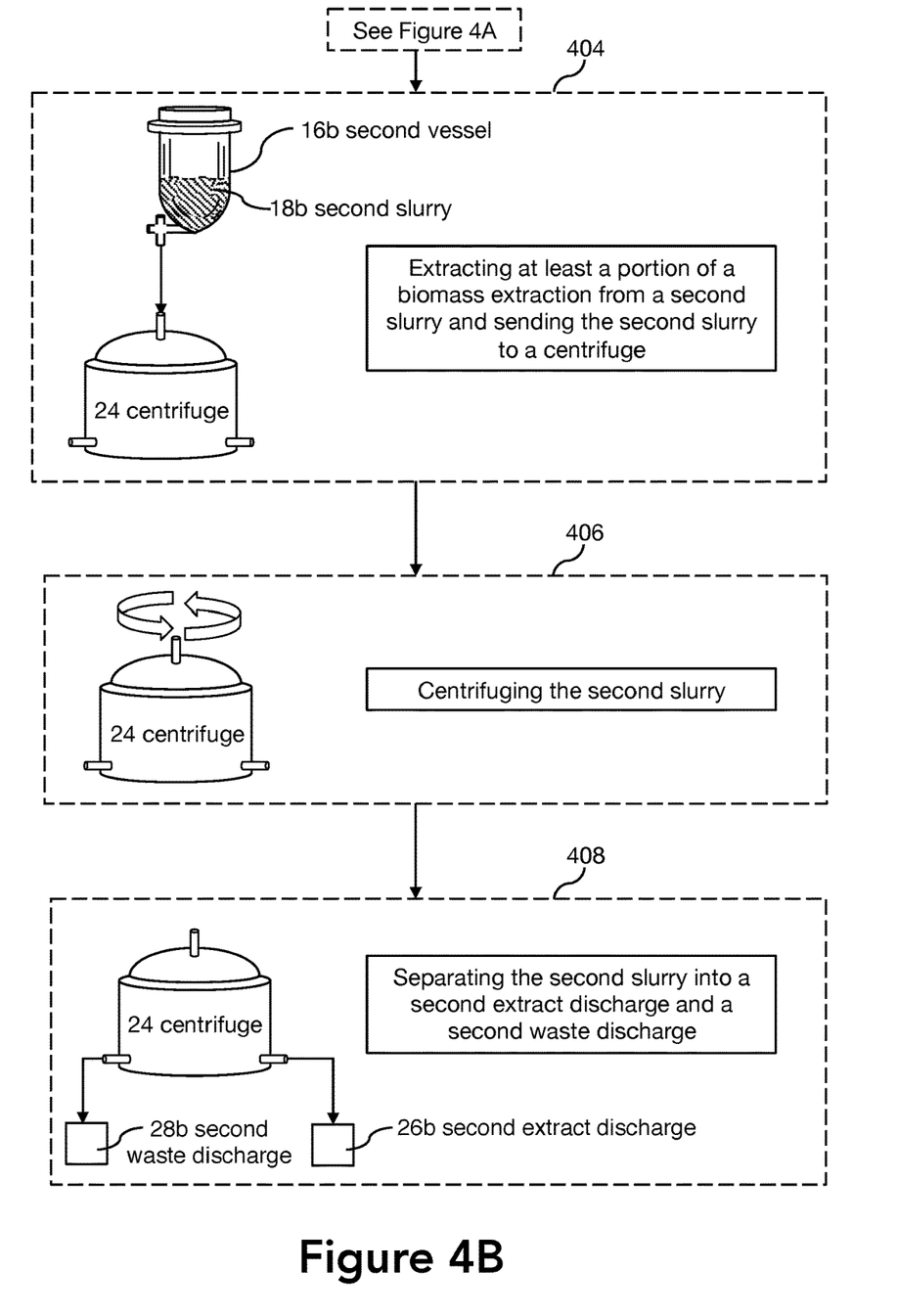
FIG. 4B illustrates a method of extracting a biomass extraction and centrifuging and separating a second slurry, according to some embodiments.

FIGS. 4A and 4B illustrate a method of continuously extracting and centrifuging biomass in a second vessel 16b, whereby FIG. 4A shows the first two steps of the method and FIG. 4B is a continuation of FIG. 4A to demonstrate the proceeding steps of the method. In some embodiments, the method includes sending biomass 20 from a biomass feed tank 12 into the second vessel 16b and sending solvent 22 from a solvent feed tank 14 into the second vessel 16b (at step 400). As such, FIGS. 4A and 4B illustrate the idea of how multiple vessels 16 may be used to simultaneously perform various process steps to maintain a continuous or quasi-continuous process. In many embodiments, FIGS. 4A and 4B should be understood in sequence with FIGS. 3A and 3B, as the second vessel 16b of FIGS. 4A and 4B goes through the method steps immediately following the first vessel 16a of FIGS. 3A and 3B. The method steps in FIGS. 4A and 4B may overlap in time with the method steps of FIGS. 3A and 3B. For example, sending step 400 may occur simultaneously with holding step 302.

With continued reference to FIGS. 4A and 4B, the biomass 20 and solvent 22 may then be held in the second vessel 16b for a predetermined amount of time (at step 402). In many embodiments, the biomass 20 and solvent 22 form a second slurry 18b in the second vessel 16b. The method may further comprise extracting at least a portion of a biomass extraction from the second slurry 18b and sending the second slurry 18b to a centrifuge 24 (at step 404). The method may further comprise centrifuging the second slurry 18b (at step 406) and separating the second slurry 18b into a second extract discharge 26b and a second waste discharge 28b (at step 408).

In many embodiments where the plurality of vessels 16 comprises a number greater than two vessels, the method illustrated in FIGS. 3A-4B is repeated in the additional vessels of the plurality of vessels 16, until at least one of the biomass and solvent feed tanks 12, 14 is substantially empty. For example, in an embodiment where the plurality of vessels 16 comprises four vessels, the method steps shown in FIGS. 3A-4B are carried out in the third and fourth vessels, subsequently. In many embodiments, this repetition will cover multiple cycles of the extraction and centrifugation process, wherein each vessel 16 will continuously go through the sending, holding, extracting, centrifuging, and separating steps multiple times. Due to the overlap in time of different method steps in different vessels 16, in many embodiments one or more vessels 16 operate in a second cycle while one or more of the other vessels 16 are still completing a first cycle. In this way, the method may allow for a higher production capacity and increased efficiency over the prior art methods of extracting and centrifuging biomass.

Figure 5:
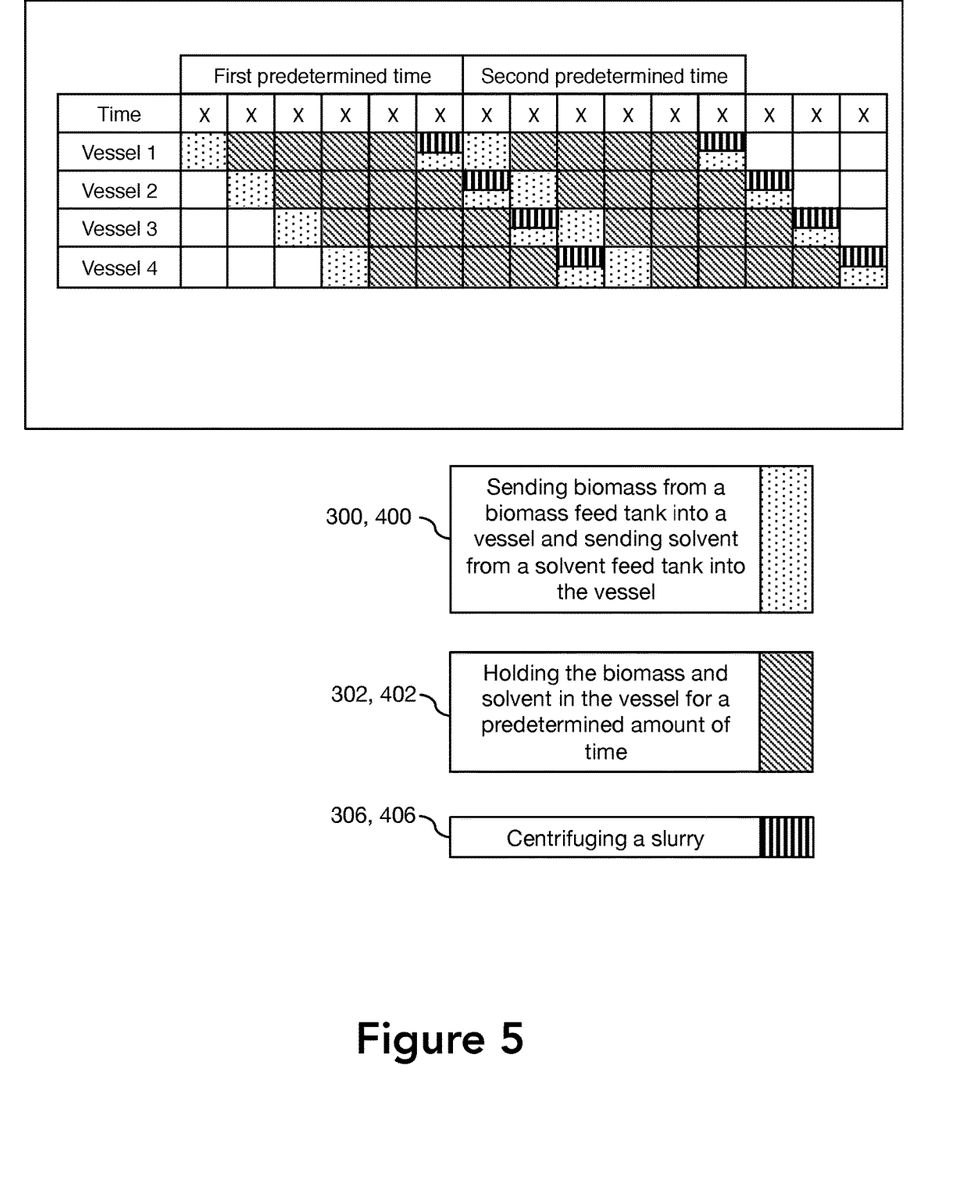
FIG. 5 illustrates a graphical interpretation of a method of continuously extracting and centrifuging biomass, according to some embodiments.

FIG. 5 illustrates a graphical interpretation of a method of continuously extracting and centrifuging biomass, and shows how the method progresses over time, according to some embodiments. The graph illustrates the steps of sending the biomass 20 from the biomass feed tank 12 into the vessel 16 and sending the solvent 22 from the solvent feed tank 14 into the vessel 16 (at steps 300 and 400), holding the biomass 20 and solvent 22 in the vessel 16 for a predetermined amount of time (at steps 302 and 402), and centrifuging the slurry 18 (at steps 306 and 406). In many embodiments, the holding step 302, 402 also comprises extracting the biomass 20 extraction into the slurry 18. The centrifuging step 306, 406 may also comprise separating the slurry 18 into the waste discharge 28 and extract discharge 26. The steps may proceed in the following order: sending biomass 20 and solvent 22 into the vessel 16 (300, 400); holding the biomass 20 and solvent 22 in the vessel 16 (302, 402); and centrifuging the slurry 18 (306, 406). Following the centrifuging step 306, 406, the method steps may repeat for additional cycles. In some embodiments, the centrifuging step 306, 406 of a first cycle occurs simultaneously with the sending step 300, 400 for a second cycle of the same vessel. Accordingly, and as previously discussed, the repetition of steps may allow the method to operate in a continuous manner.

FIG. 5 includes a "first predetermined time" and a "second predetermined time". It is important to note that the first and second predetermined times are different than the previously discussed "predetermined amount of time" in which a slurry is held in a vessel. The first predetermined time may define a total length of time of the biomass extraction and centrifugation process, as it extends from the initial sending biomass 20 and solvent 22 at step 300 through the centrifuging the slurry 18 at step 306 for a first cycle of Vessel 1. The second predetermined time encompasses the same steps, but for a second cycle of the process. As mentioned above, the overall biomass extraction and centrifugation method may comprise multiple cycles wherein each vessel of the plurality of vessels 16 may undergo each step of the method until at least one of the biomass feed tank 12 and the solvent feed tank 14 is substantially empty.

In some embodiments, the first predetermined amount of time substantially equals the second predetermined amount of time. Alternatively, the first predetermined amount of time may not equal the second predetermined amount of time. In some embodiments, the first predetermined amount of time and/or the second predetermined amount of time are equal to any amount of time less than 1 hour. However, in some embodiments, the first predetermined amount of time and/or the second predetermined amount of time are equal to any amount of time greater than or equal to 1 hour. This amount of time, combined with the minimal user intervention needed throughout the process, indicates that the process may run upwards of a dozen times a day, resulting in a high production capacity.

The graphical representation of FIG. 5 further illustrates that, in some embodiments, the centrifugation steps 306, 406, occur substantially simultaneously with the sending the biomass 20 and solvent 22 from feed tanks 12, 14 into the respective vessel 16 (steps 300, 400) and the holding the biomass 20 and solvent 22 in the vessel 16 for a predetermined amount of time (steps 302, 402). In many embodiments, as the first slurry 18a from the first cycle of the first vessel 16a is in the centrifuge, biomass 20 and solvent 22 are sent to the first vessel 16a to begin a second cycle of the biomass extraction and centrifugation process. In some embodiments, while the first slurry 18a of the first cycle of the first vessel 16 is being centrifuged the second 16b, third, and fourth vessels may be holding the biomass 20 and solvent 22 (at step 302, 402) (and thus extracting the biomass extraction) of the first cycle. Generally, the upshot of FIG. 5 is that multiple process steps may be occurring substantially simultaneously to thereby promote the continuous operational aspects of the systems and methods disclosed herein.

Figure 6:
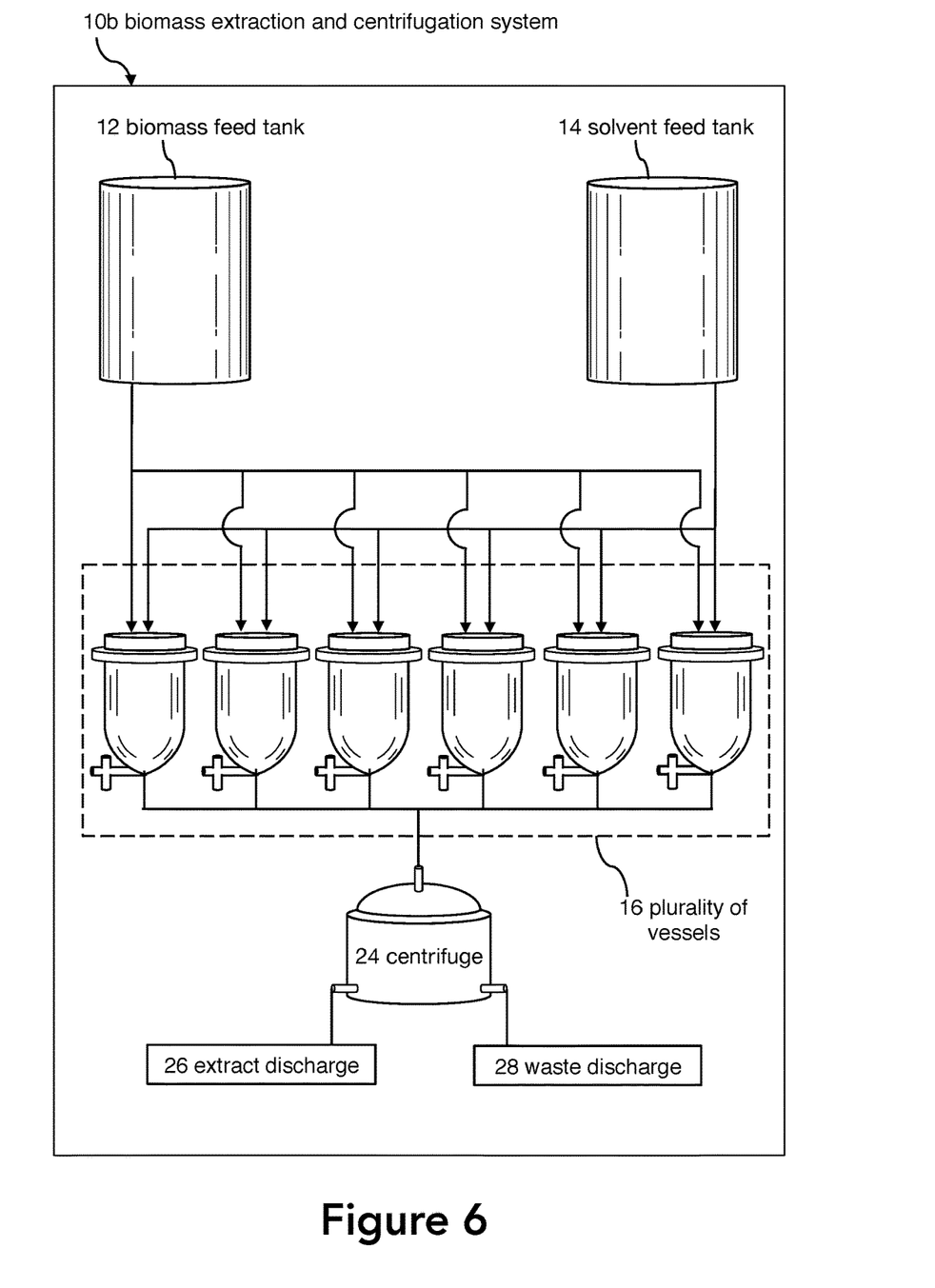
FIG. 6 illustrates a schematic view of a biomass extraction and centrifugation system, according to some embodiments.

FIG. 6 illustrates the same schematic view of the biomass extraction and centrifugation system 10b as FIG. 1, with the exception that FIG. 6 shows an embodiment of the system 10b where the plurality of vessels 16 comprises six vessels, rather than four. FIG. 6 also shows the biomass feed tank 12, solvent feed tank 14, centrifuge 24, extract discharge 26, and waste discharge 28. Though an embodiment of the system 10b wherein the plurality of vessels 16 comprises four vessels is used as an example throughout the disclosure, FIG. 6 demonstrates that, in some embodiments, the plurality of vessels 16 comprises more than four vessels. In several embodiments, the plurality of vessels 16 comprises a number of vessels other than four or six; these numbers were chosen as simple examples to depict the variability possible in the number of vessels. It is conceivable that the system 10b may, in some embodiments, include a plurality of vessels 16 comprising up to twenty or thirty vessels.

A number of vessels in the plurality of vessels 16 may be determined by both the predetermined amount of time for holding the biomass and solvent and centrifugation time for each slurry 18, as well as by the amount of biomass 20 and solvent 22 in the feed tanks 12, 14, and the capacity of the centrifuge 24. It is important to note that the size, as well as the number, of vessels 16 is variable in the system 10b. As previously discussed, the size of the vessels 16 may be determined by the batch size of the centrifuge 24. The variability in the number of vessels 16 may allow the system 10b to be used for extraction and centrifugation processes involving different amounts and/or types of biomass 20 and solvent 22, and under the appropriate conditions (holding time, centrifugation time, etc.), for the chosen biomass 20 and/or solvent 22. The system 10b is highly adaptable to work with biomass extraction and centrifugation processes across different industries and conditions, and the variability in the number of vessels 16 is one of the chief elements of that adaptability.

The following parameters are included to illustrate only one example of the system 10 performing the method steps previously discussed. These parameters in no way are meant to apply to all possible embodiments of the system 10 and/or method, and are included entirely for the sake of providing a detailed description of the system 10 and method in operation. In this embodiment, the biomass is cannabis or hemp, and the solvent (liquid) is ethanol.

Basket capacity of centrifuge: 400 liters (solid biomass)
Specific gravity of wet material fed into centrifuge: 0.5 kg/dm$^3$
Net amount of wet biomass fed into centrifuge with liquid: 200 kg
Expected residual moisture of biomass after centrifugation: 2%
Specific gravity of biomass after centrifugation: 0.2 kg/dm$^3$
Amount of biomass discharged after centrifugation: 80 kg
Dry biomass per extraction batch: 80 kg
Typical biomass to liquid ratio: 1:5
Required liquid amount per extraction batch: 400 kg
Specific gravity of solvent: 0.789 kg/liter
Required liquid volume per extraction batch: 507 liters
Typical extraction time in vessel: 12 minutes
Additional time for charging and discharging of the vessel: 4 minutes
Typical centrifuge batch time: 4 minutes Standard centrifugation uses centrifugal force to facilitate the separation of liquids from solids. Centrifugal force is generated by spinning a sample—in the case of this disclosure, a slurry—at high speed to separate the desired component. Hydraulic pressure is created by liquid moving through the cake (the remaining waste discharge 28 may be referred to as "cake"), and once the liquid is removed there is no hydraulic pressure. While standard centrifugation is generally very effective, spinning and centrifugal force alone can only remove so much moisture from a sample.

Pressure Added Centrifugation (PAC) introduces another pressure force to the centrifugation process in order to remove any liquid that would typically be left behind after a standard centrifugation process, as the leftover liquid usually isn't enough to generate its own hydraulic pressure to separate from the biomass. In the context of this disclosure, a PAC system may be used to drive additional moisture from the solvent (e.g. ethanol) out of the biomass material (e.g. cannabis). This step may be beneficial not only to obtain a better centrifugation result and extract as much solvent and biomass extract as possible, but it may also result in a safer waste material. In some embodiments, the waste discharge produced by the systems and methods of this disclosure comprises cannabis with some residual ethanol and ethanol vapors, which are flammable. Centrifugation with the PAC system drives off the residual ethanol and ethanol vapors, resulting in an inert waste discharge where disposal is easier and safer than for a waste discharge containing residual ethanol.

In some embodiments, the centrifuge 24 used to carry out the centrifugation step 306, 406 comprises a PAC system. The PAC system may be installed onto an existing centrifuge 24, and may be located near a feed pipe of the centrifuge 24. In many embodiments, the PAC system injects pressurized gas, such as nitrogen or air, through the feed pipe into the bowl of the centrifuge 24 while the centrifuge 24 is spinning. Gas injection may occur anytime after the filling cycle is complete, and may occur before or after the final spin cycle. In some embodiments, the injected gas is pressurized to 40 pounds per square inch (psi). However, the gas may be injected at any pressure from atmospheric pressure up to 90 psi.

In many embodiments, the PAC system operates at ambient temperature. Alternatively, the PAC system may heat the gas prior to injection in order to achieve a vaporizing effect on residual moisture in the biomass materials in the centrifuge. When heated, the temperature may reach about 95° C. to 120° C., depending on what can be withstood by the centrifuge materials. The temperature range may also depend on what is appropriate and safe for the sample materials inside the centrifuge, particularly in cases where the solid, not the liquid, is the desired result. In many embodiments, the PAC system is installed onto the centrifuge 24 and engaged when necessary. This allows the PAC system to remain on a centrifuge even when standard centrifugation, without PAC, is sufficient for a particular centrifugation process.

Interpretation

Although certain embodiments and examples are disclosed above, inventive subject matter extends beyond the specifically disclosed embodiments to other alternative embodiments and/or uses, and to modifications and equivalents thereof. Thus, the scope of the claims appended hereto is not limited by any of the particular embodiments described above. The structures, systems, methods, and/or devices described herein may be embodied as integrated components or as separate components. Furthermore, various omissions, substitutions, and changes in the form of the methods and systems described herein may be made without departing from the spirit of the inventions disclosed herein.

The section headings and subheadings provided herein are nonlimiting. The section headings and subheadings do not represent or limit the full scope of the embodiments described in the sections to which the headings and subheadings pertain. For example, a section titled "Topic 1" may include embodiments that do not pertain to Topic 1 and embodiments described in other sections may apply to and be combined with embodiments described within the "Topic 1" section.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment.

The terms "comprising," "including," "having," and the like are synonymous and are used inclusively, in an open-ended fashion, and do not exclude additional elements, features, acts, operations and so forth. Also, the term "or" is used in its inclusive sense (and not in its exclusive sense) so that when used, for example, to connect a list of elements, the term "or" means one, some, or all of the elements in the list.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require at least one of X, at least one of Y, and at least one of Z to each be present.

The term "and/or" means that "and" applies to some embodiments and "or" applies to some embodiments. Thus, A, B, and/or C can be replaced with A, B, and C written in one sentence and A, B, or C written in another sentence. A, B, and/or C means that some embodiments can include A and B, some embodiments can include A and C, some embodiments can include B and C, some embodiments can only include A, some embodiments can include only B, some embodiments can include only C, and some embodiments can include A, B, and C. The term "and/or" is used to avoid unnecessary redundancy. Furthermore, the phrase "at least one of" may be used as a shorthand way of saying "and/or". In this regard, the phrase "at least one of" may mean the same thing as "and/or".

The term "about" is used to mean approximately, and is not intended as a limiting term. For example, claim 17 includes the phrase "wherein sending biomass and solvent to the first vessel takes about 4 minutes" and in this context, "about" is not intended to limit the time to exactly four minutes. In this regard, the phrase "wherein sending biomass and solvent to the first vessel takes about 4 minutes" may be interpreted to mean that the time ranges from 2 to 10 minutes.

The term "continuous" is used to encompass continuous, semi-continuous, quasi-continuous, and/or batch processing methods. For example, claim 8 includes the phrase "a method of continuously extracting and centrifuging biomass" and in this context, "continuously" is meant to include the possibility of a continuous, semi-continuous, quasi-continuous, and/or batch method.

What is claimed is:

1. A method of using a biomass extraction and centrifugation system to continuously extract and centrifuge biomass, the method comprising:
    sending a first portion of biomass from a biomass feed tank into a first vessel of a plurality of vessels and sending a first portion of solvent from a solvent feed tank into the first vessel;
    holding the first portion of biomass and the first portion of solvent in the first vessel for a predetermined amount of time, wherein a first slurry of a first cycle comprises the first portion of biomass and the first portion of solvent;
    extracting at least a portion of a biomass extraction from the first slurry of the first cycle; and
    separating, via a centrifuge fluidly coupled to the plurality of vessels, the first slurry of the first cycle into a first extract discharge and a first waste discharge.

2. The method of claim 1, further comprising:
    sending a second portion of biomass from the biomass feed tank into a second vessel of the plurality of vessels and sending a second portion of solvent from the solvent feed tank into the second vessel;
    holding the second portion of biomass and the second portion of solvent in the second vessel for the predetermined amount of time, wherein a second slurry of the first cycle comprises the second portion of biomass and the second portion of solvent;
    extracting at least a portion of a biomass extraction from the second slurry of the first cycle; and
    separating, via the centrifuge, the second slurry of the first cycle into a second extract discharge and a second waste discharge.

3. The method of claim 2, further comprising extracting at least the portion of the biomass extraction from the first slurry of the first cycle while simultaneously sending the second portion of biomass and the second portion of solvent into the second vessel.

4. The method of claim 2, further comprising:
    sending a third portion of biomass from the biomass feed tank into a third vessel of the plurality of vessels and sending a third portion of solvent from the solvent feed tank into the third vessel;
    holding the third portion of biomass and the third portion of solvent in the third vessel for the predetermined amount of time, wherein a third slurry of the first cycle comprises the third portion of biomass and the third portion of solvent;
    extracting at least a portion of a biomass extraction from the third slurry of the first cycle; and
    separating, via the centrifuge, the third slurry of the first cycle into a third extract discharge and a third waste discharge.

5. The method of claim 4, further comprising:
    extracting at least the portion of the biomass extraction from the first slurry of the first cycle while simultaneously sending the third portion of biomass and the third portion of solvent into the third vessel; and
    extracting at least the portion of the biomass extraction from the second slurry of the first cycle while simultaneously sending the third portion of biomass and the third portion of solvent into the third vessel.

6. The method of claim 4, further comprising:
    sending a fourth portion of biomass from the biomass feed tank into a fourth vessel of the plurality of vessels and sending a fourth portion of solvent from the solvent feed tank into the fourth vessel;
    holding the fourth portion of biomass and the fourth portion of solvent in the fourth vessel for the predetermined amount of time, wherein a fourth slurry of the first cycle comprises the fourth portion of biomass and the fourth portion of solvent;
    extracting at least a portion of a biomass extraction from the fourth slurry of the first cycle; and
    separating, via the centrifuge, the fourth slurry of the first cycle into a fourth extract discharge and a fourth waste discharge.

7. The method of claim 6, further comprising:
    extracting at least the portion of the biomass extraction from the first slurry of the first cycle while simultaneously sending the fourth portion of biomass and the fourth portion of solvent into the fourth vessel;
    extracting at least the portion of the biomass extraction from the second slurry of the first cycle while simultaneously sending the fourth portion of biomass and the fourth portion of solvent into the fourth vessel; and
    extracting at least the portion of the biomass extraction from the third slurry of the first cycle while simultaneously sending the fourth portion of biomass and the fourth portion of solvent into the fourth vessel.

8. The method of claim 6, wherein while extracting at least the portion of the biomass extraction from the fourth slurry of the first cycle, the method further comprising separating the first slurry of the first cycle via the centrifuge, sending a fifth portion of biomass from the biomass feed tank into the first vessel for a second cycle, sending a fifth portion of solvent from the solvent feed tank into the first vessel for the second cycle, and extracting at least a portion of a biomass extraction from the first slurry of the second cycle.

9. The method of claim 6, wherein while separating the fourth slurry of the first cycle, the method further comprising:
    extracting at least a portion of a biomass extraction from the first slurry of a second cycle;
    extracting at least a portion of a biomass extraction from the second slurry of the second cycle;
    extracting at least a portion of a biomass extraction from the third slurry of the second cycle; and sending an eighth portion of biomass from the biomass feed tank into the fourth vessel of the plurality of vessels for a second cycle and sending an eighth portion of solvent from the solvent feed tank into the fourth vessel for a second cycle.

10. The method of claim 1, wherein sending the first portion of biomass and the first portion of solvent to the first vessel takes about 4 minutes, the predetermined amount of time is about 12 minutes, and the first slurry is centrifuged for about 4 minutes.

11. The method of claim 10, wherein a number of vessels in the plurality of vessels is determined by both the predetermined amount of time for holding a respective portion of biomass and solvent and centrifugation time to separate each slurry.

12. The method of claim 11, wherein the number of vessels in the plurality of vessels is further determined by an amount of biomass in a biomass feed tank, an amount of solvent in a solvent feed tank, and a capacity of a centrifuge.

13. The method of claim 8, wherein the sending, extracting, and separating steps repeat until at least one of the biomass and solvent feed tank is substantially empty.

14. The method of claim 8, further comprising:
extracting at least a portion of a biomass extraction from the second slurry of the first cycle, separating the second slurry of the first cycle via the centrifuge, sending a sixth portion of biomass from the biomass feed tank into the second vessel for the second cycle, sending a sixth portion of solvent from the solvent feed tank into the second vessel for the second cycle, and extracting at least a portion of a biomass extraction from the second slurry of the second cycle; and
extracting at least a portion of a biomass extraction from the third slurry of the first cycle, separating the third slurry of the first cycle via the centrifuge, sending a seventh portion of biomass from the biomass feed tank into the third vessel for a second cycle, and sending a seventh portion of solvent from the solvent feed tank into the third vessel for a second cycle.

15. The method of claim 1, wherein the biomass extraction and centrifugation system is sized and configured to run in a continuous manner with a constant and repeatable extraction result.

16. The method of claim 4, further comprising covering each vessel of the plurality of vessels to at least partially enclose each vessel.

17. The method of claim 1, wherein the biomass comprises hops.

18. The method of claim 1, wherein the biomass comprises at least one of cannabis and hemp.

19. The method of claim 18, wherein the biomass extraction comprises at least one of cannabidiol and tetrahydrocannabinol.

20. The method of claim 1, wherein the solvent comprises ethanol.

* * * * *